(12) United States Patent
Townsend et al.

(10) Patent No.: US 10,602,980 B2
(45) Date of Patent: Mar. 31, 2020

(54) SECURING DEVICE FOR CONNECTING TO A DISPLAY DEVICE

(71) Applicant: Fitbit, Inc., San Francisco, CA (US)

(72) Inventors: Marcus M. Townsend, San Francisco, CA (US); Mark C. Solomon, San Jose, CA (US); Steven W. Johns, Vancouver (CA)

(73) Assignee: FITBIT, INC., San Francisco, CA (US)

(*) Notice: Subject to any disclaimer, the term of this patent is extended or adjusted under 35 U.S.C. 154(b) by 0 days.

(21) Appl. No.: 16/029,312

(22) Filed: Jul. 6, 2018

(65) Prior Publication Data

US 2019/0083033 A1    Mar. 21, 2019

Related U.S. Application Data

(63) Continuation of application No. 15/180,558, filed on Jun. 13, 2016, now Pat. No. 10,016,161, which is a (Continued)

(51) Int. Cl.
*G06F 1/16* (2006.01)
*H05K 5/00* (2006.01)
(Continued)

(52) U.S. Cl.
CPC .......... *A61B 5/681* (2013.01); *A61B 5/0022* (2013.01); *A61B 5/0024* (2013.01);
(Continued)

(58) Field of Classification Search
CPC ......... G06F 1/163; H05K 5/026; A61B 5/681; A61B 5/0022; A61B 5/0024; A61B 5/02055; A61B 5/1112; A61B 5/742; A61B 5/01; A61B 5/021; A61B 5/02438; A61B 5/0531; A61B 5/14532
(Continued)

(56) References Cited

U.S. PATENT DOCUMENTS 5,008,864 A    4/1991   Yoshitake
5,889,737 A    3/1999   Alameh
(Continued)

FOREIGN PATENT DOCUMENTS

EP         2504961       10/2012
EP    002655142-0001     3/2015
EP    002655118-0001     4/2015

OTHER PUBLICATIONS

Non-Final Office Action issued in U.S. Appl. No. 14/827,075 dated Nov. 30, 2015.
(Continued)

*Primary Examiner* — Anthony M Haughton
(74) *Attorney, Agent, or Firm* — Hogan Lovells US LLP

(57) ABSTRACT

A description is provided of a wearable device that is made up of a display device and a securing device that provides at least an overlay portion to provide electrical connection to the display device. The display device and the securing device may both contain electrical circuitry. The overlay connection to the display device can create an electrical connection between the electrical circuitry on the display device and the electrical circuitry in the securing device.

20 Claims, 13 Drawing Sheets

Related U.S. Application Data continuation of application No. 14/827,075, filed on Aug. 14, 2015, now Pat. No. 9,367,087.

(60) Provisional application No. 62/127,761, filed on Mar. 3, 2015.

(51) Int. Cl.

| | | |
|---|---|---|
| *H05K 7/00* | (2006.01) | |
| *A61B 5/00* | (2006.01) | |
| *A61B 90/98* | (2016.01) | |
| *A61B 5/0205* | (2006.01) | |
| *A61B 5/11* | (2006.01) | |
| *G04B 47/00* | (2006.01) | |
| *A61B 5/01* | (2006.01) | |
| *A61B 5/021* | (2006.01) | |
| *A61B 5/024* | (2006.01) | |
| *A61B 5/053* | (2006.01) | |
| *A61B 5/145* | (2006.01) | |

(52) U.S. Cl.
CPC ........ *A61B 5/02055* (2013.01); *A61B 5/1112* (2013.01); *A61B 5/742* (2013.01); *A61B 90/98* (2016.02); *G04B 47/00* (2013.01); *G06F 1/163* (2013.01); *G06F 1/1637* (2013.01); *G06F 1/1679* (2013.01); *A61B 5/01* (2013.01); *A61B 5/021* (2013.01); *A61B 5/02438* (2013.01); *A61B 5/0531* (2013.01); *A61B 5/14532* (2013.01)

(58) Field of Classification Search
USPC .......................... 361/679.01, 679.02, 679.03
See application file for complete search history.

(56) References Cited

U.S. PATENT DOCUMENTS

| | | |
|---|---|---|
| D641,349 S | 7/2011 | Baumann |
| 8,787,006 B2 | 7/2014 | Golko |
| D733,142 S | 6/2015 | Solomon et al. |
| D743,278 S | 11/2015 | Solomon et al. |
| D745,515 S | 12/2015 | Solomon et al. |
| 9,367,087 B1 | 6/2016 | Townsend et al. |
| 10,016,161 B2 | 7/2018 | Townsend et al. |
| 2004/0023556 A1 | 2/2004 | Smith |
| 2007/0064542 A1 | 3/2007 | Fukushima |
| 2011/0053666 A1 | 3/2011 | Kang |
| 2012/0092822 A1 | 4/2012 | Mooring |
| 2013/0040610 A1 | 2/2013 | Migicovsky et al. |
| 2015/0126117 A1 | 5/2015 | Wong et al. |
| 2015/0212541 A1 | 7/2015 | Lu |
| 2015/0223033 A1 | 8/2015 | Migicovsky et al. |
| 2015/0223034 A1 | 8/2015 | Migicovsky et al. |
| 2015/0223355 A1* | 8/2015 | Fleck ...................... G06F 1/163 361/679.03 |
| 2015/0333302 A1 | 11/2015 | Johns et al. |
| 2015/0334772 A1 | 11/2015 | Wong et al. |
| 2016/0066859 A1 | 3/2016 | Crawford |

OTHER PUBLICATIONS

Notice of Allowance issued in U.S. Appl. No. 14/827,075 dated May 3, 2016.
Non-Final Office Action issued in U.S. Appl. No. 15/180,558 dated Sep. 11, 2017.
Notice of Allowance issued in U.S. Appl. No. 15/180,558 dated Mar. 19, 2018.

* cited by examiner

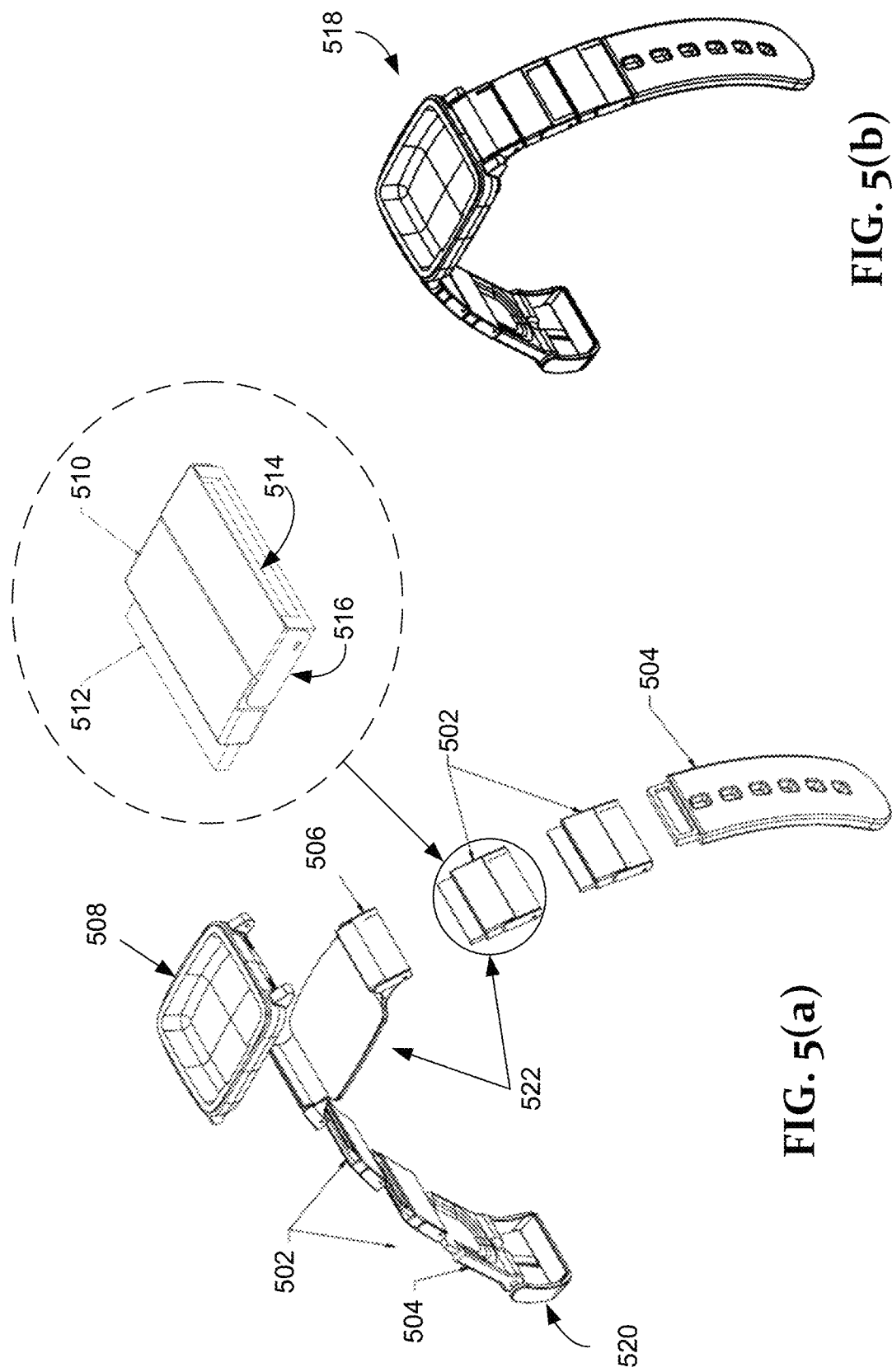

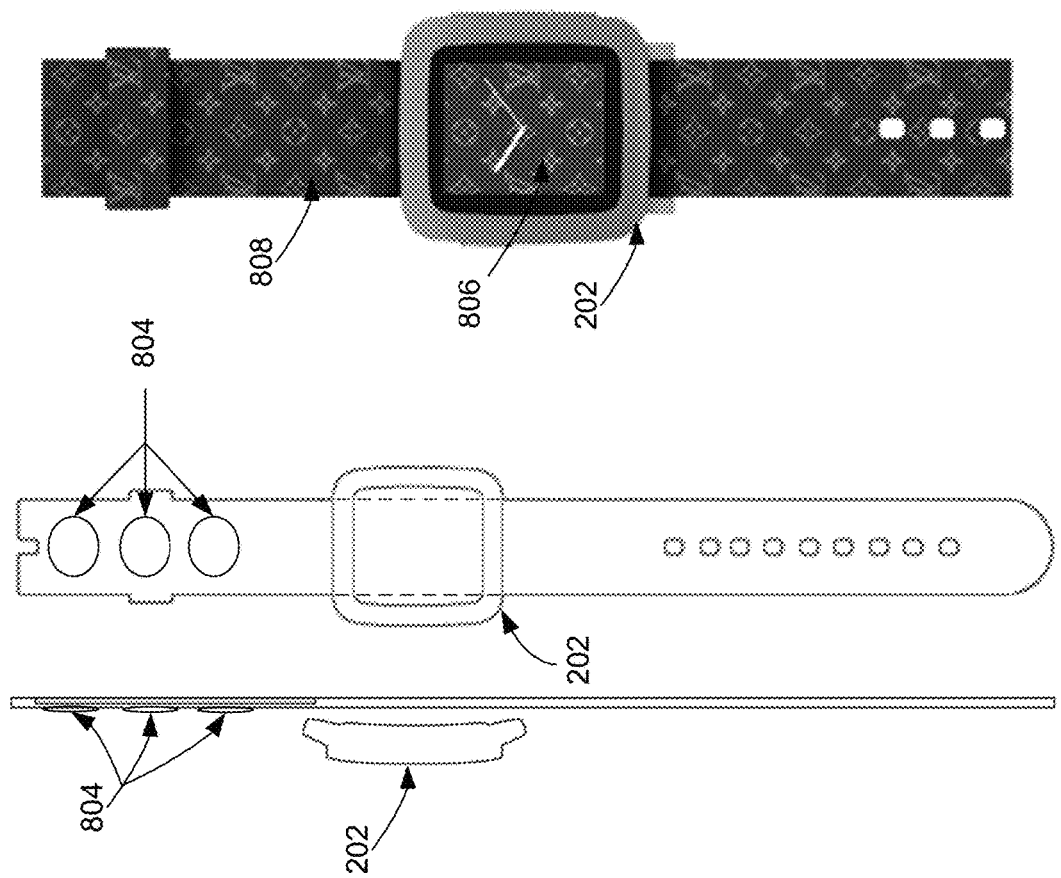
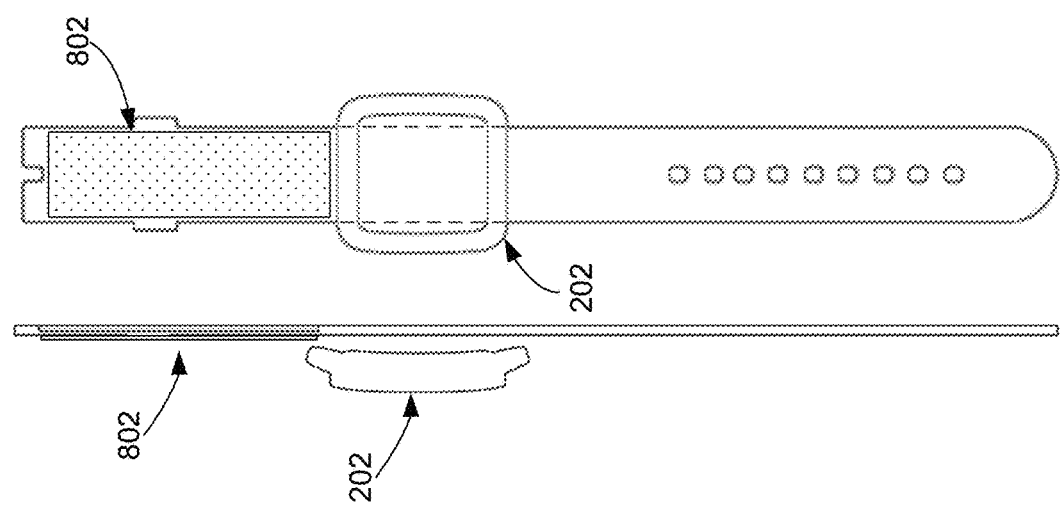
FIG. 8(a) FIG. 8(b) FIG. 8(c)

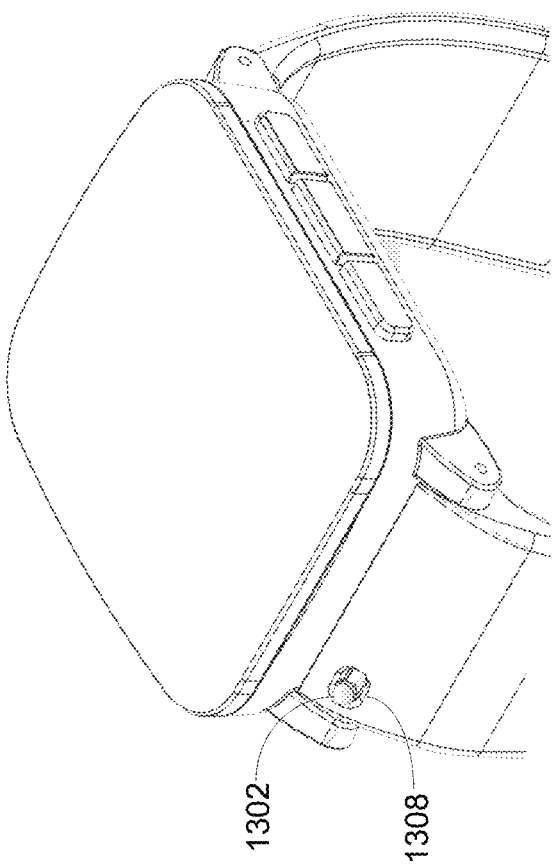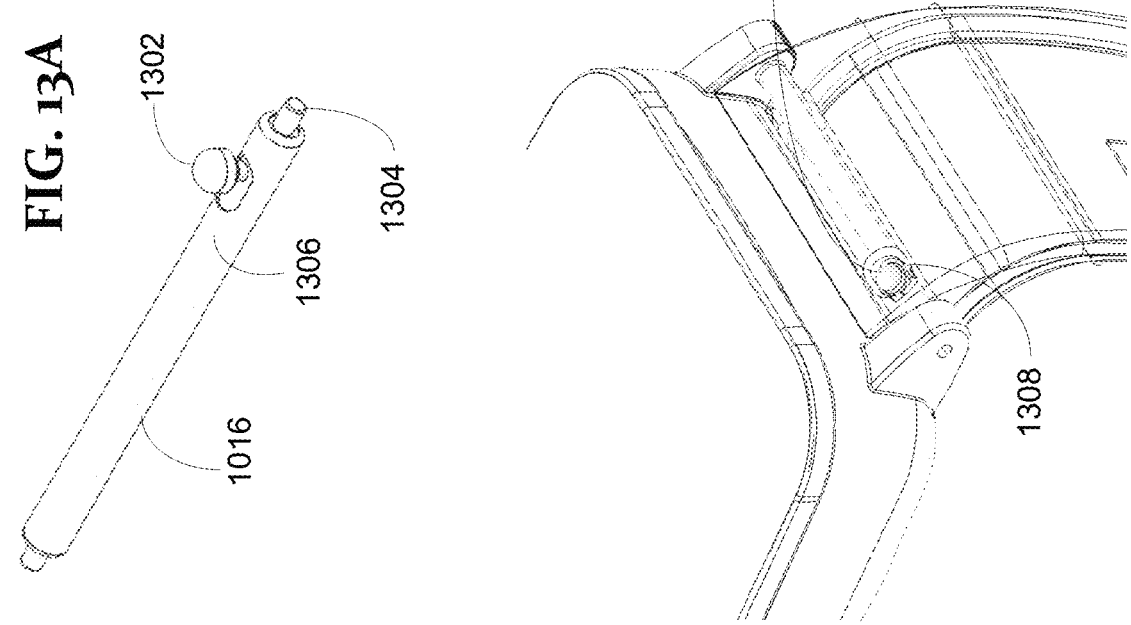

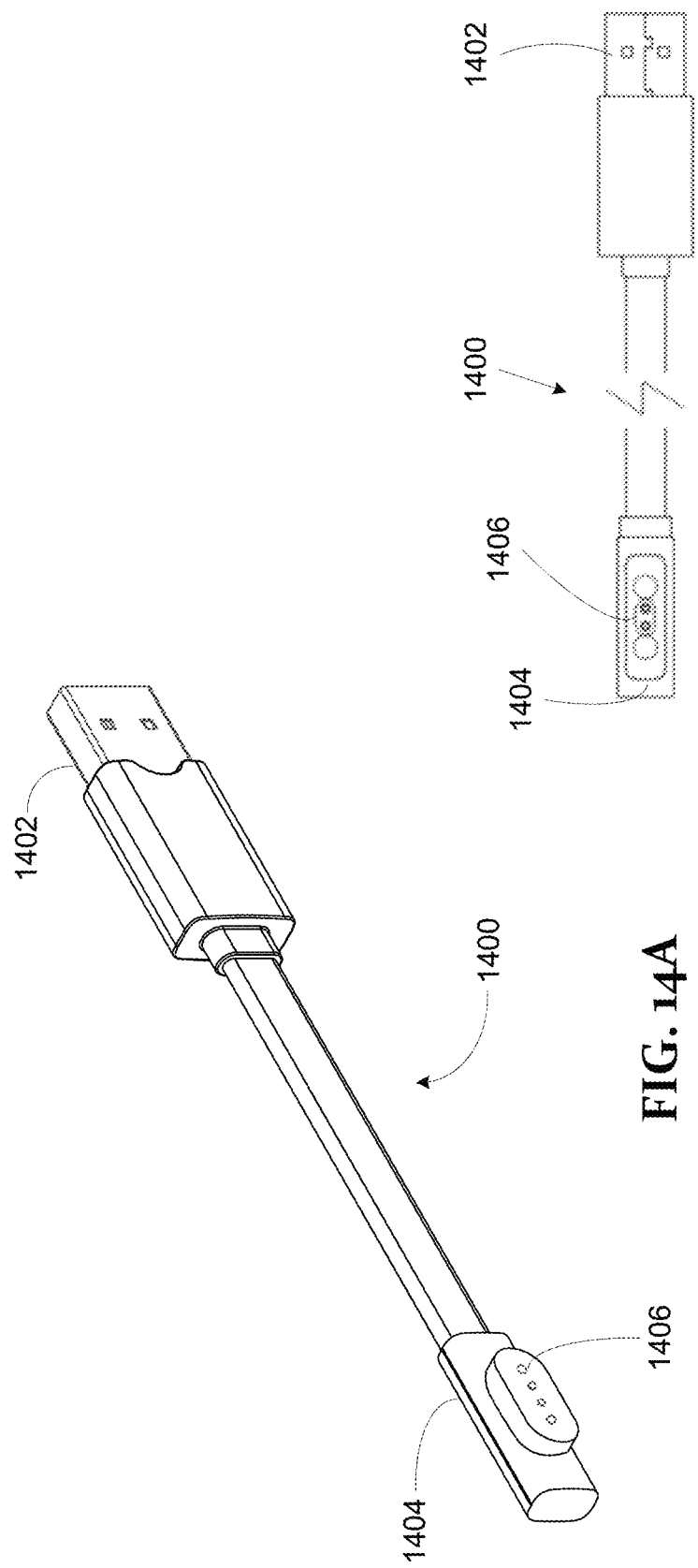

SECURING DEVICE FOR CONNECTING TO A DISPLAY DEVICE

CROSS REFERENCE TO RELATED APPLICATIONS

This Non-Provisional Application under 35 U.S.C. § 120 claims as a Continuation Patent Application priority to and the benefit of U.S. patent Title: "NOVEL SECURING DEVICE FOR CONNECTING TO DISPLAY DEVICE," application Ser. No. 15/180,558 with Filing Date Jun. 13, 2016, which claims under 35 U.S.C. § 120 as a Continuation Patent Application priority to and the benefit of U.S. Pat. No. 9,367,087, Title: "NOVEL SECURING DEVICE FOR CONNECTING TO DISPLAY DEVICE," application Ser. No. 14/827,075 with Filing Date Aug. 14, 2015, which claims under 35 U.S.C. § 119 priority to and the benefit of Provisional Patent Application No. 62/127,761, titled, "CONNECTION BY ACCESSORY DEVICE WITH INTEGRATED CIRCUITRY LAYER," filed Mar. 3, 2015, all of which are herein incorporated by reference.

BACKGROUND OF THE INVENTION

1. Field of the Invention

The invention relates generally to a method, system, and apparatus for integrating electronic circuitry into a securing device for a user device, such as a smartwatch and the like, for the purpose of augmenting the capability of the user device.

SUMMARY OF THE INVENTION

Implementations of the disclosed technology relate to wearable device 518 that may include a display device 202, such as a watch, and a securing device 265, such as a watch band. The securing device 202 may contain electronic circuitry. The wearable device 518 may be used with an external device, such as a smartphone. The technology disclosed herein can be used with any wearable device 518, including but not limited to smart necklaces, bracelets, and other devices pinned or otherwise attached to a user's clothing or body. An overlay portion of the securing device may be provided to contact a series of contacts on the back of the display device. The same contacts may be used to charge the watch when a charging cable is connected. The dual use of the contacts, if provided, simplifies the display device design by minimizing contacts needed. Various devices are disclosed to allow simple attachment and/or removal of the securing device from the display device.

BRIEF DESCRIPTION OF THE FIGURES

The accompanying drawings, which are incorporated in and constitute a part of this specification, illustrate an implementation of apparatuses and methods that together with the detailed description, serve to explain advantages and principles consistent with the invention.

FIGS. 5(a)-(b) illustrate perspective views of another embodiment in which the securing device is segmented.

FIGS. 6(a)-(c), 7(a)-(c) and 8(a)-(c) illustrate various embodiments and implementations utilizing various display devices and securing devices, for instance like those disclosed in FIGS. 2(a)-(d), 3 and 5.

FIGS. 13A-13C are various views of a quick release device for use in attaching a display device to a securing device FIGS. 14A and 14B are perspective views of an electrical power connectors that may be used with a display device, such as that shown in FIGS. 10A-10C.

DETAILED DESCRIPTION

This application claims priority to U.S. Provisional Application No. 62/127,761 filed Mar. 3, 2015, which is incorporated herein by reference in its entirety.

Figure 1:
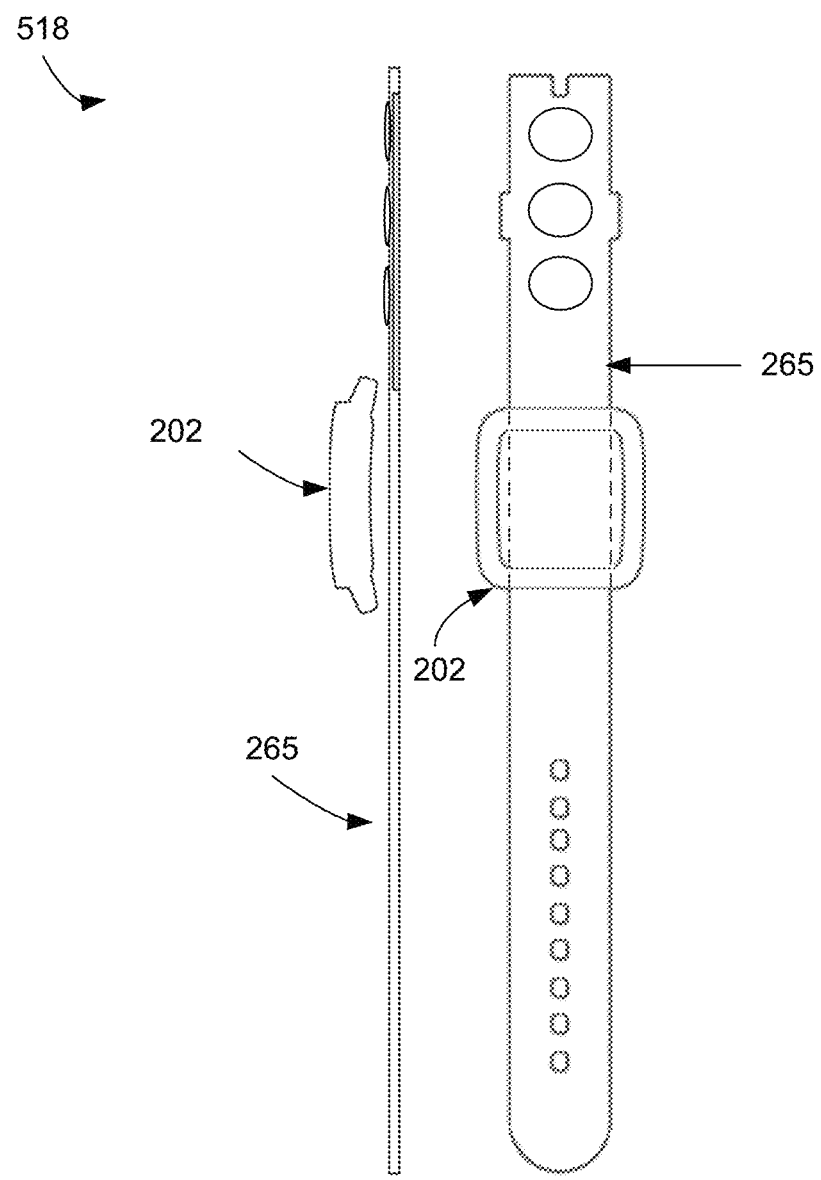
FIG. 1 illustrates a wearable device as discussed herein

Multiple variations are discussed of a wearable device 518 as shown in FIG. 1. Generally the wearable device 518 is made up of a display device 202, and a securing device, 265 to which the display device 202 may be attached. In some of the embodiments, the securing device 265 of the wearable device 518 includes circuitry that can be in communication with the display device 202, and can further expand the functionality and capability of the display device 202. While examples are given of a wearable device 518 that is a smartwatch, the wearable devices disclosed herein are useful in other formats.

With this in mind, the following description begins with a wearable device 518 with reference to FIGS. 2(a)-(d), which implements electronic circuitry into securing device where the securing device takes the form of a band. The circuitry in the securing device may be configured to perform various tasks, which will be discussed in greater detail herein. The description continues with FIG. 3, which is a cross-sectional view of an assembled wearable device 518, like that illustrated in FIGS. 2(a)-(d). Next, the description continues with the flow charts illustrated in FIGS. 4(a)-(b), which illustrate and describe two exemplary, but non-exclusive, methods of assembling and/or manufacturing a securing device, for instance, like that shown in FIGS. 2(a)-(d) and 3. Next follows the description relating to FIGS. 6(a)-(c), 7(a)-(c) and 8(a)-(c), which illustrates various embodiments of, and uses for, the wearable devices 518, like the examples disclosed in FIGS. 2(a)-(d), 3 and 5. Next follows the description related to FIG. 9, which illustrates the steps of at least one embodiment where certain events are automatically triggered by the connecting of components of the wearable device 518 from FIGS. 2(a)-(d), 3 and 5.

Figure 2:
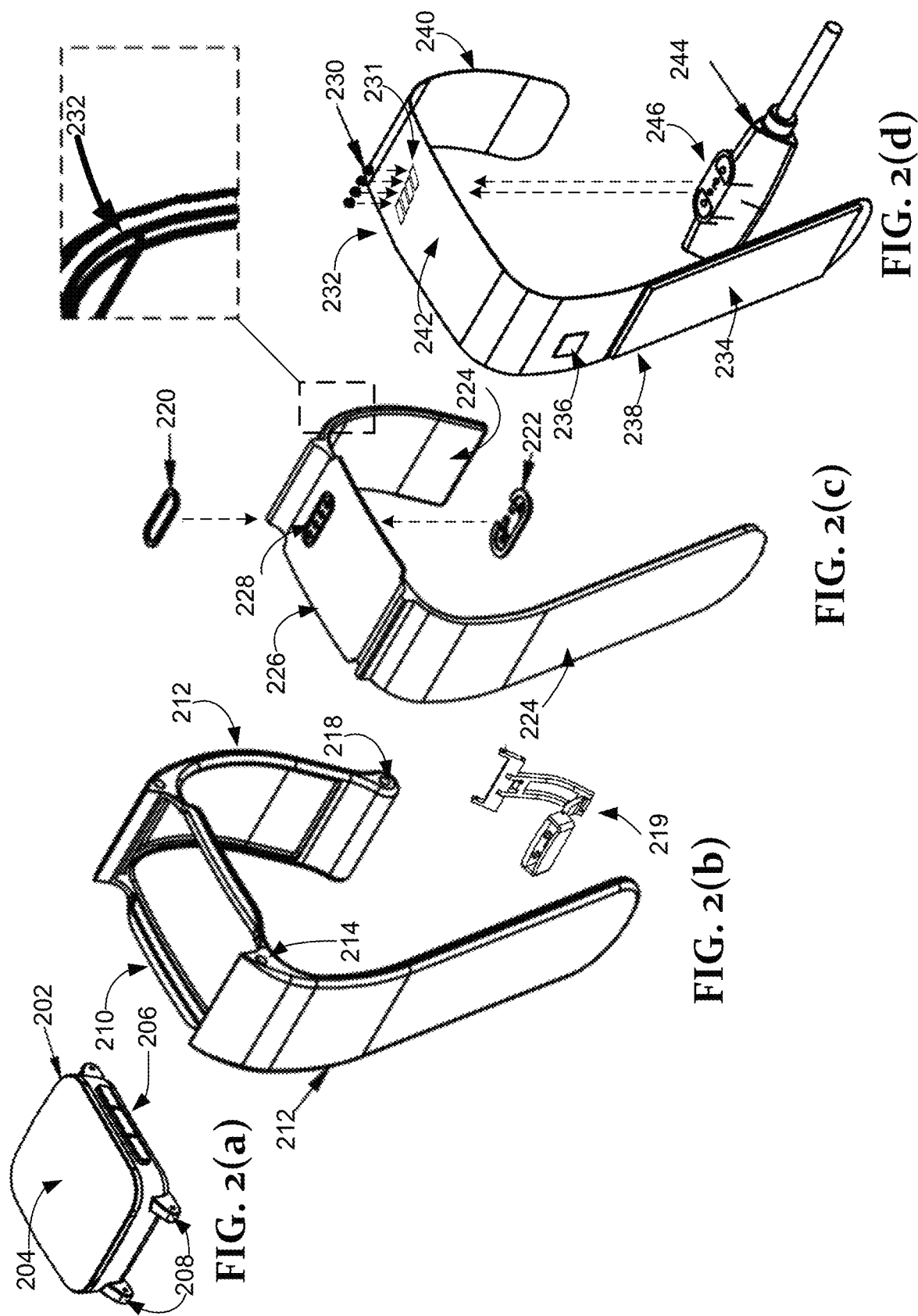
FIGS. 2(a)-(d) illustrate perspective views of various portions of one embodiment wherein securing device includes electronic circuitry configured to electronically communicate with a display device.

Turning now to FIGS. 2(a)-(d), a securing device specifically shown as a band is shown, which may be comprised of electronic circuitry configured to communicate with a display device, 202. The securing device is illustrated in three different layers, 212, 224, and 232, which may be formed together into a securing device, as later shown in FIG. 3 at 265. Turning to FIG. 2(a), a display device 202 shown by example in the form of a watch that may be a smartwatch device is illustrated. The display device 202 may contain any number of electronic components, including but not limited to a processor, memory, wireless interface (e.g., BlueTooth), charging interface (all not shown), buttons, 206, and a display, 204. The display device 202 may also be capable of communicating with an external device, such as a smartphone or tablet. In this way, the display device 202 may receive notifications from the external device to alert the user of the devices of an incoming communication or alert. In this embodiment, the display device 202 has a liquid crystal display ("LCD") 204 configured to display contents generated by the device 202. Those having ordinary skill in the art would recognize that while a LCD is illustrated in this embodiment, any other type of displays may be suitable for use with this invention, such as e-paper, electronic ink ("E Ink"), organic light-emitting diode displays ("OLED"), or active-matrix organic light-emitting diode ("AMOLED"). The display device 202 as shown contains four tabs 208, which are designed to allow the display device 202 to be attached to the securing device, 265 in FIG. 3, which will be discussed in greater detail herein. The display device 202 may include a plurality of buttons 206, which may enable a user to control the settings or functionality of the display device 202. While the buttons 206 disclosed are physical obtrusive buttons, touch sensors could be used in lieu thereof, thereby conserving space on the side of the display device 202. Alternatively, the buttons 206 could be built into the display, which could be touch based to allow a user to control the display device 202 without the need for potentially obtrusive buttons placed on other portions of the display device 202. The bottom surface (not shown) of the display device 202 may also include an interface (e.g., pogo pins) for coupling the display device 202 to the securing device, which will be discussed in greater detail herein.

Turning now to FIG. 2(b), perspective view of a first layer 212 of the securing device is shown. A first layer 212 of the band is the outer most layer of the fully assembled apparatus. The first layer 212 may be made of any material suitable to allow the securing device to be worn, such as leather, cloth, rubber, plastic, or other material. The material use can also assist in presenting a desired aesthetic. As would be understood by those having ordinary skill in the art, the type of material suitable for use as the first layer 212 may change depending on the intended use of the band. The first layer 212 may be made of plastic because of its water-resistant qualities, rendering it capable of being used in a water environment. A housing 210 is disposed between two sections of the securing device. The housing 210 may be comprised of plastic, (e.g., Polycarbonate or Polycarbonate/Acrylonitrile Butadiene Styrene), metal (e.g., steel, or aluminum) or any other material. The housing 210 is designed to receive the display device 202 such that it is firmly secured or coupled to the securing device. This may be accomplished by snapping the four tabs 208 of the display device 202 into the four receiving members 214 of the housing 210 of the securing device. The first layer 212 may include a clasp connector 218. The clasp connector 218 is designed to attach to a clamp, such as clamp 219 illustrated in FIG. 2(b). However, it would be apparent to those having ordinary skill in the art that the securing device could be closed around a user's wrist using other connections, such as a ratchet, magnet, bucket connector, fold over clasp, toggle clasp, tongue clasp, or other fastener. Depending on the type of clasp used, clasp connector 218 may not be necessitated.

Turning now to FIG. 2(c), a perspective view of a second layer 224 (e.g., Low Pressure Molded ("LPM") layer) of the securing device is shown. The second layer 224 also comprises a surface 226 interposed between two sections of the second layer 224, the surface 226 mating with the upward facing surface of the housing 210 when the first and second layers are joined together. The surface 226 is designed to allow circuitry within the securing device to interface with circuitry (e.g., the display, processor, memory, etc.) of the display device 202. A series of through holes 228 may be used to allow pins on the bottom surface of the display device 202 to electrically connect with circuitry in the securing device, which will be discussed in more detail with regard to FIG. 2(d). A rubber gasket 220 is disposed on the top of the surface 226 around the holes 228, while a steel member 222 is disposed on the bottom of the surface 226 around holes (shown as 228 in FIG. 2C), providing some sealing for the interface between the securing device and display device 202 and the securing device and other external circuitry, such as a battery charger (not shown). As will be discussed in greater detail with regard to FIG. 2(d), disposed within the second layer 224 is a third layer 232, which may be comprised of electronic circuitry, the third layer 232 being secured to the second layer 224 by an adhesive or other fastener, such as a mechanical fastener like a spring biased pin or cotter pin. In one embodiment, the second layer 224 is formed around the third layer 232, which in some instances may mean that the third layer 232 is protected from exposure to liquid.

Turning now to FIG. 2(d), the third layer 232 of the securing device is illustrated in the perspective view. The third layer 232 is comprised of electronic circuitry which may be comprised of a Polyether ether keton (PEEK), transparent conductive polyester film, Copper indium gallium selenide (CIGS), or other flexible circuit materials (FCM) known in the art. As would be understood by those having ordinary skill in the art, FCM are typically comprised of: (1) a base material (e.g., polyester (PET), polyimide (PI), Polyethermide (PEI), etc.); (2) a bonding adhesive, which constitute a flexible polymer film that provides the foundation for a laminate; and (3) a metal foil which is commonly used as the conductive element. FCM are particularly advantageous because they allow for the creation of thin, flexible, and light circuitry for use in unique applications, such as the band of a smartwatch, or similar electronics. While FCM is described, it would be understood by those having ordinary skill in the art that any type of circuitry capable of being incorporated into the securing device may be utilized, such as printed circuit board ("PCB"). The third layer 232 may be encapsulated by the second layer 224 such that the third layer 232 is protected from exposure to liquids. The third layer 232 is comprised of a first circuitry section 238, second circuitry section 240, and bridge layer 242 connecting the first circuitry section 238 and second circuitry section 240. The third layer 232 may also include a battery 234 capable of electronically connecting to display device 202 to act as the exclusive source of power or as an additional source of power. Alternatively, the battery 234 may act as a backup in case a battery of the display device 202 loses its charge. The battery 234 may be a Prologium Flexible Battery, ultrathin zinc-polymer battery, flexible lithium ion battery, Flexible Lithium-Ceramic Battery (FLCB) or other battery material. In some instances it is beneficial for the battery 234 to have sufficient flexibility to allow the securing device to freely bend without damaging the battery 234.

The third layer 232 may communicate with the display device 202 and/or other electronic circuitry, such as battery charger 244, via any suitable interface. The charger 244 comprises a connector 246 sufficient to allow the charger 244 to maintain electric connectivity to the third layer 232 and/or the display device 202 via a flat mating surface. The mating surface 231 may be a flat copper surface or plurality of surfaces (i.e., an upward facing and downward facing surface) on or embedded within both sides of third layer 232, wherein the copper surface(s) are capable of receiving: (1) electronic interface pins protruding downward from the bottom of external device 202 and/or (2) electronic interface pins protruding upward from the charger 244 or other electronic devices. In this manner, the display device 202 and charger 244 (or other electronic circuitry) may be connected to the securing device alone or in combination. The connector 246 may also include magnets to aid it in interfacing with the downward facing portion of the mating surface 231. In this way, a user will not be required to physically snap or latch the connector 246 to the securing device, which may be tedious and difficult given that the downward facing portion (not shown) of the mating surface 231 for the charger connection may be on the bottom of the housing 210. The display device 202 may have pins 230 protruding downward from its bottom for interfacing with the upward facing portion of the flat mating surface 231 of the third layer 232 via through-holes 228. Specifically, a user may insert the display device 202 into the housing 210 by snapping the display device 202 in place via the protruding members 208 and receiving member 214, so that the pins 230 (in particular the pins can be pogo pins) protruding from display device 202 engage with the upward facing portion of the mating surface 231 of the third layer 232. Likewise, the upward facing pins of the battery charger 246 may then be connected to the downward facing portion (not shown) of the flat mating surface 231 on the third layer 232. While in this embodiment pins 230 and a flat mating surface 231 on third layer 232 are utilized to facilitate communication between the display device 202 and securing device, it would be understood by those having ordinary skill in the art that any type of connector known in the art for coupling electronics may be used.

The third layer 232 may also include one or more miscellaneous circuits 236 configured to perform a variety of functions. The miscellaneous circuitry 236 may be configured to: (1) GPS track; (2) monitor health (e.g., skin resistance, heart rate/pulse sensor, and skin temperature); (3) receive/transmit wireless signals (e.g., for Wi-Fi, BlueTooth, Near Field Communication ("NFC"), Radio Frequency Identification ("RFID")); (4) emit audible, vibratory, light shock, or visual signals; (5) act as an additional display (e.g., a small LCD display or a plurality of LEDs forming a display); (6) provide additional memory; (7) record/output audio or process audio commands to control the securing device or display device 202; (8) charge a BlueTooth headset; (9) automatically tighten the securing device to the precise size of the user's wrist using a material such as PolyPower DEAP material, which expands and contracts with electricity; (10) allow a user to create their own circuitry on the exterior of the securing device using, for example, a breadboard; (11) allow a user to control the securing device or display device 202 using a touch sensor on the securing device; (12) allow a user to charge or communicate with the securing device and/or display device 202 via an end of the securing device that comprises an interface (e.g., a USB interface); (13) automatically configure or control the display device 202 and/or allow the display device 202 to automatically configure or control the circuitry layer 232; and (14) fingerprint ID using the securing device.

Figure 3:
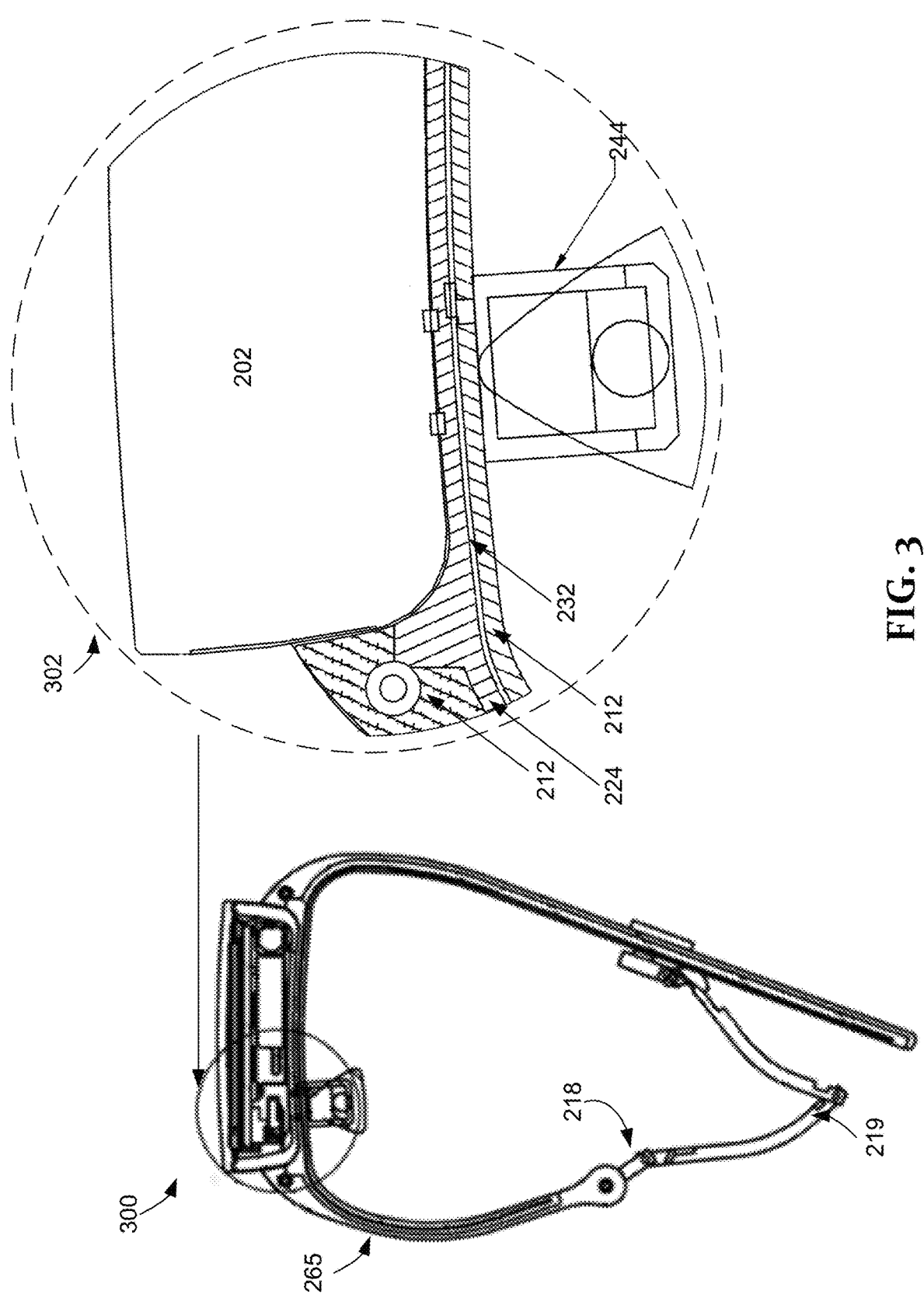
FIG. 3 illustrates a cross-sectional view of the embodiment illustrated in FIGS. 2(a)-(d), whereby the portions in that embodiment are shown assembled into a wearable device.

Turning now to FIG. 3, a cross-sectional view of the full assembly of the assembled wearable device 518 from FIGS. 2(a)-(d) is illustrated. Full cross-sectional view 300 is illustrated with detailed view 302 focused on the central portion of the securing device 265 and display device 202. As shown, the first layer 212 is the outer most visible layer of the securing device 265, while the third layer 232 is interposed within second layer 224. The display device 202 is secured within housing 210 via receiving members 214 (not shown). Charging connector 244 is coupled to the third layer 232 and display device 202 via pins (not shown). A foam gasket may be used to seal around the pins.

Figures 4A, 4B:
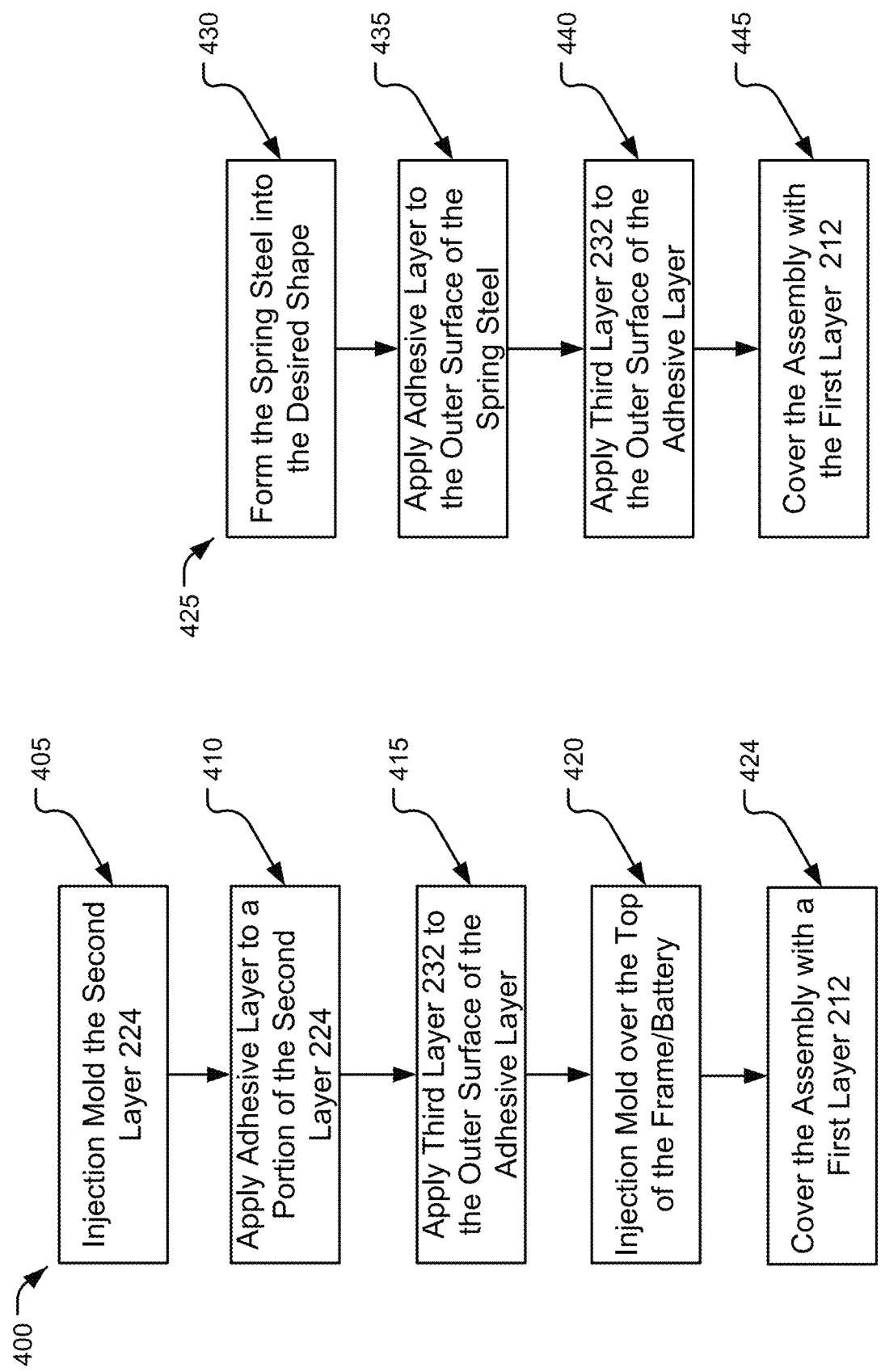
FIG. 4(a)-(b) illustrate flow charts for methods of assembling the apparatus of FIGS. 2(a)-(d) and 3.
Figures 6A, 6B, 6C:
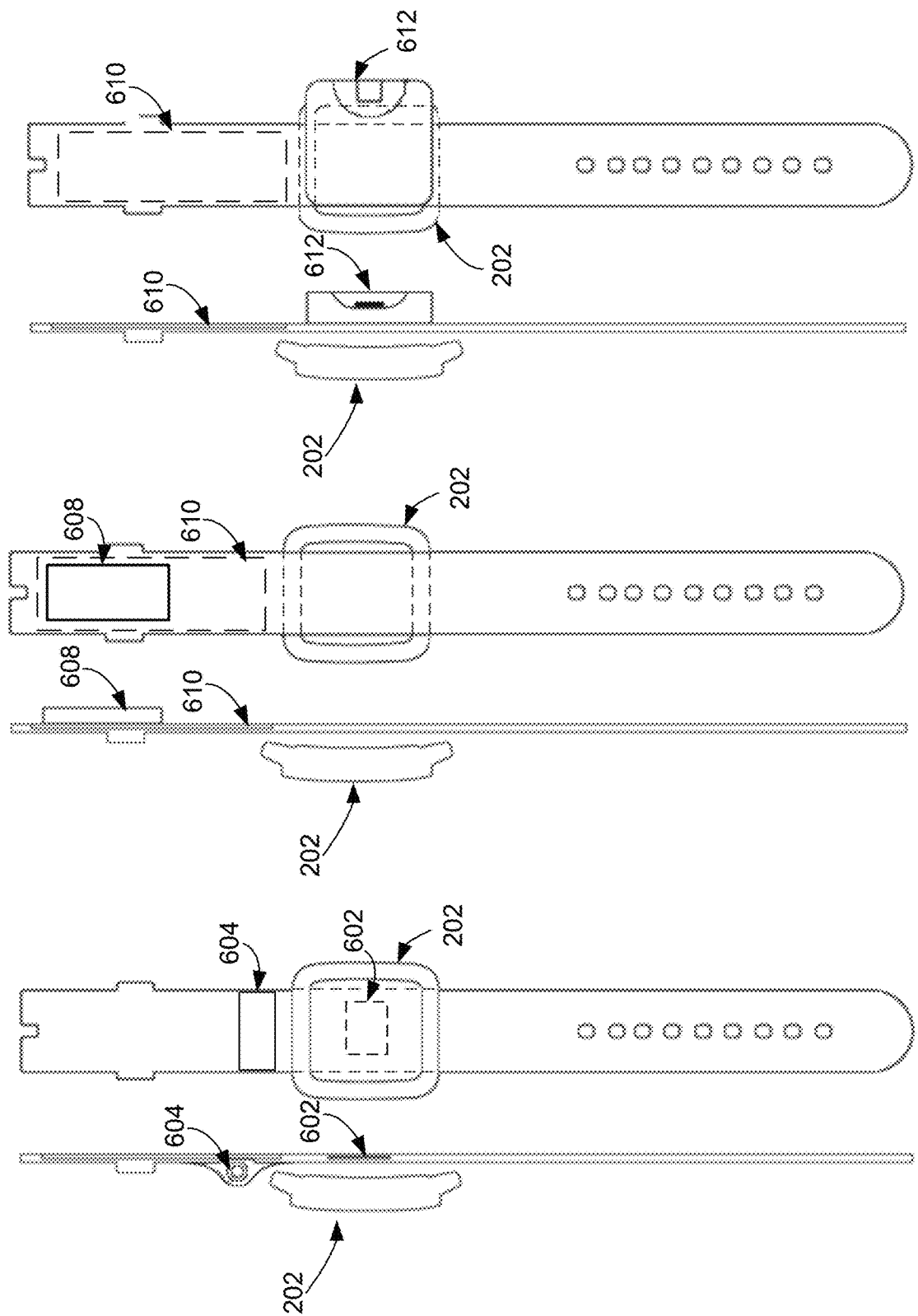
Figure 7C:
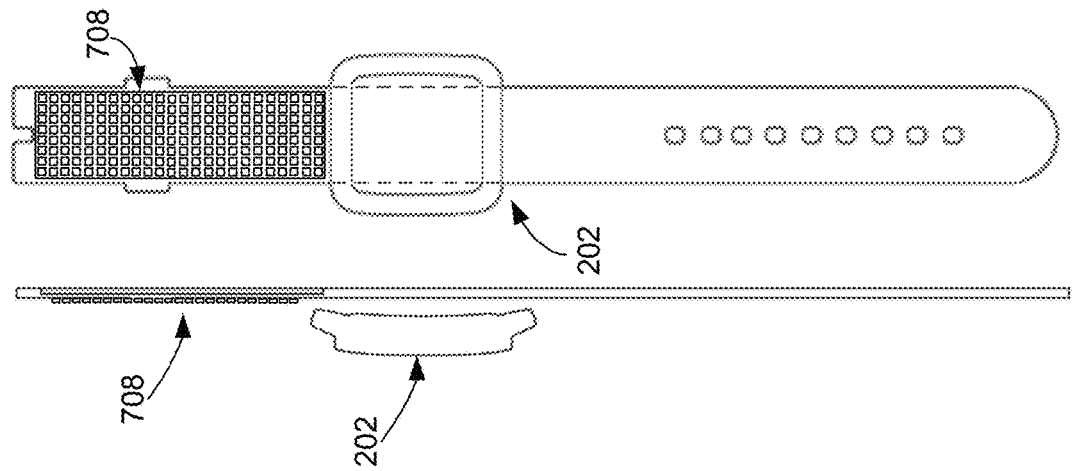
Figure 7B:
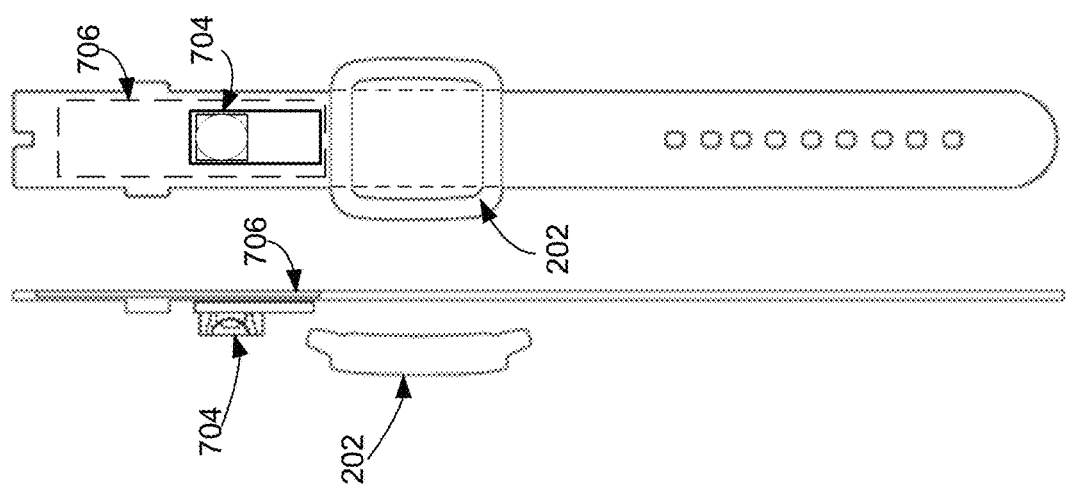
Figure 7A:
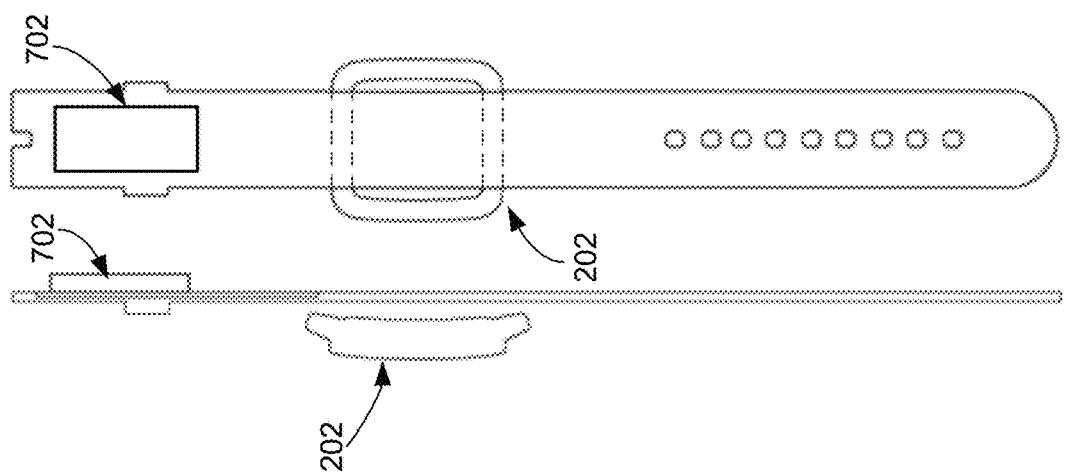

Turning now to FIGS. 4(a)-4(b), flowcharts illustrating exemplary methods of assembling the apparatus from FIGS. 2(a)-(d) and 3 are shown. It should be noted initially that the methods 400 and 425 are simplified flowcharts to represent useful processes but they do not limit the sequence in which the functions take place or even the functions that may take place in order to achieve the apparatus from FIGS. 2(a)-(d) and 3. Indeed, those having ordinary skill in the art would understand that the apparatus can be formed using any molding technique, such as compression molding, transfer molding, injection molding, insert molding, and/or double shot injection molding.

As shown, the manufacturing process 400 starts at step 405 which may include the forming of the second layer 224, by injection molding, which would generally be performed using a polymer, but may alternatively include a metal (e.g., steel). Injection molding may be less flexible than utilizing spring steel as the base structure. Next, at 410 an adhesive layer is applied to a portion of the second layer 224. The adhesive layer may be comprised of any material suitable to secure the third layer 232 to the adhesive layer. At step 415, the third layer 232 is secured to the second layer 224 using the adhesive layer from step 410, for example double-sided tape. Finally, at step 420 the assembly of the circuitry layer 232, adhesive layer, and portion of second layer 224 are overmolded, to create a further portion of the second layer 224. The second layer 224 therefore encapsulates the third layer 232, containing the circuitry. The first layer 212 may then be applied to the assembly 424, which may comprise steel, leather, or another material (i.e., a fabric layer). If it is desired to use a chain-link type material (or any material that has openings) as the first layer 212, it may be helpful to first overmold the adhesive layer and the third layer 232 before applying the chain-link material (i.e., a fabric layer). This may ensure that the circuitry layer 232 is protected from liquid exposure.

While not expressly illustrated in the manufacturing process 400, a hole may be left in the top center of a portion of the overmolded second layer 224 of the securing device. Thermoplastic polyurethane (TPU) may then be injection molded or a hard material may be low pressure molded over the exposed center portion to form a water-resistant seal where the housing 210 is secured to the securing device 265. The housing 210 may then be secured to the center portion of the securing device 265 using any number of ways known in the art, which were previously discussed. Alternatively, also as previously discussed, the housing 210 may be fully integrated into the band by overmolding the housing 210 into the securing device 265. Additionally, a clasp, such as clasp 219, may be attached to one end of the securing device. The fastener may be designed to allow one end of the securing device to clamp to the opposing end of it without the need for holes in the band.

In yet another embodiment of a manufacturing process, the manufacturing process 425 starts at 430 possibly with the forming of a spring steel frame, which would be part of the second layer 224, into a desired shape for the band. Spring steel is very flexible but will typically return to its original form. Therefore, the spring steel frame must generally be initially formed into the desired shape prior to implementing it into the securing device 265. Additionally, because spring steel attempts to revert to its original form, it may be necessary to form the spring steel frame for an intended wearer's wrist size (e.g. "large wrist size," "medium wrist size"). Next, at step 435 an adhesive layer is applied to the spring steel frame. At step 440, the third layer 232 with any circuitry is secured to the spring steel frame using the adhesive layer. The second layer 224 therefore encapsulates the spring steel structure, adhesive layer, and third layer 232. Finally, at step 445 the assembly of the third layer 232, adhesive layer, and spring steel frame are covered with the first layer 212. Alternatively, the second layer 224, adhesive layer, and third layer 232 may be overmolded and then covered with the first layer 212. As previously discussed, the first layer 212 may also be comprised of a harder material, such as stainless steel. Such materials may be desirable by some wearers because of the more expensive appearance of the material.

The second layer 224 can be made with polymer or other material (e.g., a metal) suitable to achieve the objectives of a securing device with circuitry third layer 232 containing circuitry. Moreover, while adhesives are described, those of skill in the art would recognize that any method of securing the circuitry to another structure may be used. Further, while certain embodiments may be described as being water-resistant, it would be understood that it is not required.

Rather than using a unitary securing device, the securing device may be comprised of numerous sections or modules, as shown in FIG. 5(*a*). More specifically, the securing device may be comprised of a plurality of modules 502 and 504, each module containing a portion of the third layer 232 previously discussed. Each of these modules may be assembled in accordance with the manufacturing processes previously discussed, whereby the third layer 232 (e.g., containing circuitry) is within the second layer 224 (e.g., overmolded layer), and then a first layer 212 is applied. A module based securing device may be desired over a unitary securing device because each module may contain certain miscellaneous circuitry of the third layer for handling different functions. For example, one module may contain circuitry for GPS, while another module contains circuitry for monitoring certain health parameters of the wearer. Such a configuration may be useful when a wearer is planning on jogging. Conversely, when the wearer is planning on attending a social event, the wearer may elect to replace the health monitoring module with a module configured to emit audible, visual, or vibratory signals. Moreover, the display device and securing device may be configured to communicate to one another and reconfigure each other based on the specific module connected as part of the securing device. For example, when the GPS module is connected as part of the securing device, the display device may download a GPS related application or automatically start such application if the application is already on the display device.

Turning to FIG. 5(*a*) in more detail, a securing device 522 is comprised of modules 502, 504 in disconnected form. The modules 502, 504 are connected to the main body 506 of the securing device 522, which is configured to receive a display device (not shown) via display device housing 508. The modules 504 comprise the open ends of the securing device and include a connector 520 that connects one open end of the securing device to the other open end. While a generic clasp 520 is illustrated as the connector the securing device around the wearer's wrist, it would be understood that any of the previously discussed and described connectors could be used instead. Each of modules 502 and/or 504 may contain a portion of the third layer 232 which may include miscellaneous circuitry configured to handle a particular function or a plurality of functions.

Turning now to the zoomed in perspective view of a module 502, the module 502 has an overmolded body 51*o*, a thinner flexible printed circuit portion 512 that has been overmolded, a receiving portion 514, and a clip 516. The receiving portion 514 receives the flexible printed circuit portion of another module so that electrical conductivity may be established across the connected modules. The clip 516 allows the received flexible printed circuit to be secured within the receiving portion 514. While not shown here, a first layer 212 may also be applied to each portion of the modules, or a single first layer piece may be added to cover the entire assembled securing device. When fully assembled, the securing device and display device form a single wearable device 518, as illustrated in FIG. 5(*b*). As previously stated, however, each module may be replaced by another module containing circuitry that performs a function different than that of the module that was replaced.

Turning now to a more detailed discussion of the potential functionality of the third layer 232, miscellaneous circuitry 236 may comprise GPS circuitry that may allow a user to see their precise location on the display device 202 or track particular fitness related parameters, including, but not limited to, distance traveled and duration of the travel. As shown in FIG. 6(*a*), the GPS tracking circuitry 602 may be placed, for example, behind the display device 202. The GPS tracking circuitry may comprise, a GPS chip that is passive or active. The GPS circuitry 602 may then communicate with the display device 202 via third layer 232 when the display device 202 is secured in the housing 210 of the securing device. Additionally, the securing device may include an audio input 604 for connecting it or display device 202 to a headset or other output device. In this way, a user of the connected securing and display devices may track particular fitness related parameters while listening to music or the radio.

With regard to the health monitoring functionality of the miscellaneous circuitry 236, such functionality may allow a user to track certain health parameters, including but not limited to heart rate/pulse, skin resistance, skin temperature, blood pressure, and glucose levels. The miscellaneous circuitry 236 could be integrated into any portion of the third layer 232, though it is understood that certain health sensors that exist currently may be more accurate if placed in direct or close contact with certain portions of a user's body. For example, turning to FIG. 6(*b*), placement of a heart rate/pulse sensor 608 on or around the radial artery of the wearer (i.e., on the bottom of the wrist) may improve the accuracy of health sensor readings. A battery 610 may be integrated into the circuitry layer 232 to provide power to the sensor or other components of the securing device or display device 202. Similarly, other portions of the user's body may be more suitable for direct contact with a health sensor for detecting skin resistance, which may help indicate psychological or physiological changes in the user. Such a measurement may allow the wearer to review his health status over the course of a day to determine which events caused him or her more stress or anxiety. The user may then make appropriate lifestyle changes to reduce that stress or anxiety, if possible. The wearable device 518 may include the use of a blood glucose monitor, as illustrated in FIG. 6(*c*). The blood glucose monitor 612 may be coupled to the bottom of the housing 210. The glucose monitor 612 may also be removable and interchangeable with other health monitoring components, such as the heart/pulse rate sensor 608 previously discussed.

With regard to the wireless receiving/transmitting functionality of the miscellaneous circuitry 236, such circuitry may include, but is not limited to, RFID, BlueTooth, NFC, and Wi-Fi circuitry. The circuitry necessary for these technologies may be embedded into the third layer 232 of the securing device. With regard to RFID, Wi-Fi, and BlueTooth, placement of the circuitry may not be as important as the placement of the NFC circuitry, as RFID, Wi-Fi, and BlueTooth are capable of communicating at moderate distances. NFC, on the other hand, has a very limited range and the location of the NFC circuitry on the band may affect the comfort level of the wearer when attempting to use the securing device for purposes of establishing NFC with another device. A user may utilize NFC to establish communication with NFC enabled card readers to make payments. This may allow a wearer to access a digital wallet on the wearer's cellular telephone without having to actually pull the cellular telephone out to establish an NFC connection. For example, turning to FIG. 7(*a*), the miscellaneous circuitry 236 may include an NFC chip 702. This may allow the NFC chip to communicate with other portions of the third layer 232, the display device 202, and/or another device. RFID may act essentially as a "bar code," which may be used for numerous purposes, such as security clearance. For instance, a wearer of the securing device may gain access to his or her place of work by simply wearing a securing device containing the RFID circuitry. This negates the need for the wearer to pull out a clearance or access card every time he or she enters their place of work. Alternatively, the circuitry 236 may comprise BlueTooth circuitry to allow the user to couple the display device 202 to a cellular phone or other device. This may conserve space in the display device 202. While NFC, RFID, and Bluetooth have been discussed herein, it would be understood by those having ordinary skill in the art that any wireless circuitry may be utilized within the securing device to allow for data to be transferred between wireless devices.

With regard to the illumination functionality of the miscellaneous circuitry 236, such circuitry may include an LED flashlight capable of illuminating an area in a dark environment. For example, turning to FIG. 7(*b*), the LED flashlight 704 may be coupled to the third layer 232, but protrude through the first layer 212 and second layer 224. The flashlight may utilize a battery 706 embedded into the third layer 232. The battery 706 may be sufficient to provide 120 hours of life to the flashlight 704, while the flashlight 704 may illuminate at 13K-15K millicandelas ("MCD") and require a 4.5V battery.

With regard to the audible, visual, and/or vibratory indication functionality of the miscellaneous circuitry 236, such circuitry may allow a user to more conveniently determine when a certain event has been triggered by the wearable device 518 and/or a corresponding network device (e.g., a smartphone). For example, a plurality of vibratory motors may be implemented in the securing device as the miscellaneous circuitry. When the user receives a cellular telephone call, the user may be notified by a vibration originating from a single vibratory motor in the third layer 232. When the user receives a text message, the user may be notified by two vibrations originating from two separate vibratory motors spaced apart on the third layer 232. In yet another example, a user may be notified that a particular person has called by receiving three vibrations originating from three vibratory motors spaced apart on the third layer 232; while another person's call may be indicated by two vibrations originating from two vibratory motors spaced apart on the third layer 232. Alternatively, rather than having a certain number of motors vibrate together to indicate a particular caller or type of notification, the motors may vibrate sequentially to create a circular vibration pattern in one direction for one particular caller or type of notification, and in another direction for a different particular caller or type of notification. Likewise, visual indicators, such as light emitting diodes (LEDs), may be utilized in a similar manner to convey the same information to the user. For example, turning to FIG. 7(*c*), a plurality of LEDs 708 arranged in a matrix may be built into the third layer 232 and protrude through the first layer 212 and second layer 224 so that the LEDs may be visible to the user. When an alert or notification is received on the user's cellular telephone, the LEDs on the securing device may illuminate to indicate the identity of the caller or the contents of the message being received. As would be understood by those having ordinary skill in the art, the arrangement and sequencing of the speaker(s), vibratory motor(s), and visual indicator(s) may be arranged or configured in any way suitable to inform a user that particular event or notification has occurred. Alternatively, a speaker, vibratory motor, and/or visual indicator may be implemented in the securing device in lieu of the same circuitry that would normally be integrated into the display device 202. This may conserve space in display device 202. It would be understood that any functionality typically found in a display device 202 may be located instead in the securing device.

With regard to the additional memory functionality of the miscellaneous circuitry 236, such circuitry may allow a user to store additional information. For example, given the general size constraints of wearable devices 518 such as smartwatches due to a lack of available space for memory, most smartwatches are significantly limited as to the number of applications they may store as compared to smartphones. However, by storing additional memory in the securing device, a user may store significantly more applications. Moreover, a larger number of pictures, video, and/or music could also be stored in the memory of the watch if the securing device includes additional memory. Alternatively, all of the memory of a display device 202 could be stored in the securing device, which would save space in the display device 202.

With regard to the functionality for allowing users to create their own external circuitry on the securing device, the third layer 232 may be configured to communicate with a first layer 212 on the outer most surface of the securing device which includes a breadboard structure which comprises the miscellaneous circuitry 236. For example, turning to FIG. 8(*a*), an outer circuitry layer 802 in the form of, for example, a breadboard, may be electrically connected to a third layer 232. The outer circuitry layer 802 may be on the outer surface of the first layer 212 and allow a user to add their own circuitry to improve the functionality to the securing device. For example, a user may implement their own custom LED arrangement and program the securing device or display device 202 to illuminate the LED arrangement as desired.

An additional feature may be a plurality of buttons disposed along the length of the securing device. For example, turning to FIG. 8(b), buttons 804 may be incorporated into the securing device via the third layer 232. The buttons 804 may be physical buttons that slightly protrude from the outer surface of the securing device, or a touch sensor that is completely integrated and embedded into the securing device. An embedded touch sensor may be particularly advantageous, as it may reduce the overall size of the securing device as compared to physical buttons that may protrude. The buttons or touch sensor may be disposed on a small portion of the securing device, or wrap around the entire length of the securing device. Buttons or a touch sensor may allow a user to more easily control the functionality of the securing device or display device 202. For instance, a user may stop or play a song on a display device utilizing the buttons 804. As yet another example, a user may answer a telephone call utilizing the buttons 804 when the display device or securing device is coupled to a cellular telephone physically or wirelessly.

With regard to the additional display integrated into the securing device, the securing device may include several displays spaced apart along the length of the securing device, or a single, long, flexible display disposed along a length of the securing device. The circuitry 236 of the securing device display 802 may be incorporated as part of the third layer 232. The securing device display 802 may allow a user to set the appearance of the securing device based on a theme desired by the user. Moreover, as will be discussed in greater detail below, the display in the securing device may automatically program itself to visually correspond to the user interface theme of the display device 202. Conversely, the display device 202 may automatically configure its user interface to visually correspond to the theme of the securing device.

With regard to the functionality of a microphone and/or speaker included in the third layer 232, this functionality may be advantageous for several reasons. First, it may allow a wearer to accept cellular phone calls on the display device 202 itself by enabling the wearer to use the microphone and speaker to communicate with a caller. Second, the microphone may allow the user to utilize voice based commands to operate the display device 202, the securing device, and/or a corresponding cellular phone wirelessly coupled to the securing device or display device 202.

With regard to the functionality of charging a BlueTooth headset, the first and second layers 212 and 224 may be designed to hold or secure a tiny BlueTooth headset to the exterior of the securing device. For example, a very small latching device or protrusion (not shown) on the strap may be implemented that is capable of holding a tiny BlueTooth headset. The third layer 232 may be configured to charge a small ultra-capacitor of the BlueTooth headset, the headset only activating when separated from the holding mechanism of the securing device.

Yet another potential feature is the capability to charge the securing device or display device via a free end of the securing device. For example, either free end of the securing device may comprise a universal serial bus ("USB") connector, which is electrically coupled to the third layer 232 to allow the user to establish a communication link between an external device, such as a laptop, and the securing device or display device 202 secured in the housing 21o. Alternatively, the USB connector may enable the securing device to be charged by another external device, such as a laptop.

The disclosed embodiments may also include circuitry that allows the securing device or display device to be inductively charged or passively charged using RF. More specifically, inductive charging uses an electromagnetic field emanated from, for example, a charging pad in order to charge the display device or securing device without connecting them to a charger via a physical interface connector. Similarly, passive charging via RF (e.g., PowerCast RF harvesting) may allow the display device and/or securing device to harvest the energy from radio frequency waves and provide additional charging capabilities.

An additional feature is the capability of the third layer 232 to automatically cause an event on the display device 202 when the display device 202 is secured to the housing 210 and electrically coupled to the third layer 232. For instance, in reference to FIG. 8(c), the user interface 806 of the display device 202 may automatically be configured to display a "Louis Vuitton" style theme when a securing device having a "Louis Vuitton" theme 808 is connected. Such a feature would allow a user to own various securing devices, wherein each securing device has different visual characteristics and automatically causes the user interface of the display device to match or correspond to the visual characteristics of the particular securing device being used. As yet another example, a user may utilize a securing device corresponding to a particular sports theme (e.g., Dallas Cowboys), which automatically causes the display device 806 user interface to visually correspond to that particular sports theme. In yet another example, a user may have a securing device designated as a "sports strap," which may be more durable and water resistant. When a user attaches such a securing device to the display device 202, certain sports related applications (e.g., heart rate monitor, distance tracker) and/or themes are loaded by the display device 202, or if such applications are not on the display device 202, those applications may automatically be downloaded by the securing device and/or display device 202. While numerous examples of such auto-configuration have been set forth, it should be understood that the disclosure is in no way intended to be limited to those particular embodiments. Indeed, the securing device itself could be configured to cause any program, setting, or action to occur when interfaced with the display device 202, depending on the particular characteristics of the securing device.

Conversely, the display device 202 may cause the securing device to change its configuration. For example, when the display device 202 is secured within the housing 210 and electrically couples to the third layer 232, the display device 202 may cause LEDs on the securing device to illuminate to indicate a successful connection. In yet another example, if the third layer 232 comprises a securing device display, the securing device display may be set to display a theme corresponding to the theme of the user interface 806 of the display device 202 when the display device 202 and securing device are first electrically coupled.

Notably, any or all of these features may be implemented into the same securing device. For example, many of these features may be implemented utilizing a plurality of miscellaneous circuits 236, each of which is configured to add additional functionality as discussed above. Moreover, rather than having a single third layer 232, there may be multiple layers containing circuitry, each layer having its own miscellaneous circuitry 236. For example, one third layer 232 may be reserved exclusively for battery circuitry and be disposed along the entire length of the band, while an additional third layer 232 may be reserved for a plurality of miscellaneous circuits 236. It would be apparent to those having ordinary skill in the art that any number of layers of circuitry may be utilized, and that additional functionality could be implemented into the securing device. For example: (1) air bladders could be integrated into the securing device and inflate to help a user cope with motion sickness; (2) a gyroscope could be integrated into the securing device to allow the user to control the securing device or an display device using hand or arm gestures; (4) vibratory motors within the securing device could vibrate to indicate that a user is not on the correct GPS path; (5) health parameters of the wearer of the securing device could be detected/monitored and automatically be sent to emergency medical services utilizing the securing device and/or display device; (6) a breathalyzer could be implemented into the securing device; and/or (7) a drink tester sensor, which would analyze the composition of any drink and display the composition on the display device (see e.g., Vessyl drink analyzer)

Figure 9:
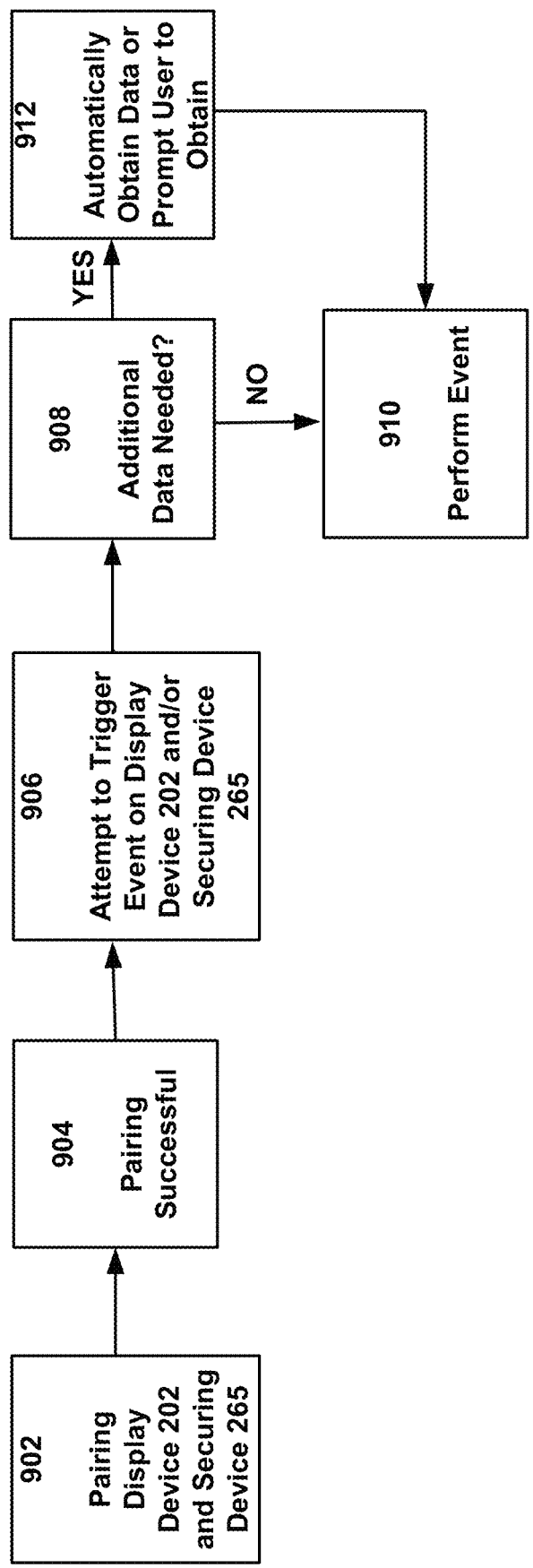
FIG. 9 illustrates a flow chart disclosing communication with or between components of a wearable device in FIGS. 2(a)-(d), 3 and 5, whereby certain functions are automatically performed based on the connection or attachment of a display device and a securing device.

Turning now to FIG. 9, a flow chart illustrating the process of triggering an event based on the coupling of the display device 202 and securing device is disclosed. When the display device 202 is first secured within the housing 21o, the display device 202 and third layer 232 attempts to electronically pair at step 902. After pairing is successful at step 904, an event is triggered on the display device 202, the securing device, or both at step 906. The event may be, for example, the configuring of the appearance of the theme on the user interface of the display device 202 based on the theme of the securing device. Conversely, the event may be configuring of the appearance of a display on the securing device based on the theme of the display device 202. At step 908 it is determined whether additional data is needed to perform the event. If no additional data is needed by either the securing or display device 202 to perform the event, the process continues to step 91o where the event is performed. However, if, for example, the event cannot be performed because of a lack of data, the data is either automatically obtained or the user is prompted to decide whether to obtain the data at step 912. For example, if the event is the changing of the theme of the display device 202 user interface theme, but the theme is not present in the memory of the display device 202, the theme may be automatically downloaded or the user may be prompted to download the theme at step 912. Once the theme is downloaded, the process moves to step 91o where the event is performed. As yet another example, a user may begin pairing a fitness securing device and display device 202 at step 902. If pairing is successful at step 904, the securing device may attempt to trigger an event on the display device 202 at step 906 by automatically running certain fitness related apps. If the apps are already on the display device 202 at step 908, the fitness related apps would automatically run at step 91o. However, if the fitness apps are not on the display device 202 at step 908, the fitness apps would either automatically download or the user would be prompted to download the apps at step 912. While only two examples are given here, it would be apparent to those having ordinary skill in the art that the securing device and/or display device 202 could be configured to trigger any event on the securing device and/or display device 202. Moreover, the user could program the trigger settings using an interface on either the display device 202 or the securing device itself. Additionally, the user may cause any event to occur upon the pairing of a particular combination of securing device and display device. Also, the disclosed process may apply (as previously discussed) when a particular module 502 or modules of the securing device are connected to the display device or to another module. For example, the connection of a module 502 relating to GPS tracking may trigger an event or action to occur on the display device. Conversely, the connection of the GPS module 502 may cause an event or action to occur on the GPS module 502 itself. Similarly, the connection of multiple modules 502 as part of the securing device may cause an action to occur that would otherwise not occur when the multiple modules 502 are connected individually. For example, the connection of a module 502 relating to GPS tracking and health status monitoring may cause a jogging application to be downloaded and activated on the display device, whereas the connection of the GPS module 502 for health status monitoring alone would not cause that event or action to occur.

While the figures show the securing device as a band in many instances it would be understood by those having ordinary skill in the art that other types of securing devices may be used. For example, a bike helmet may include integrated circuitry and be used as a securing device to receive a display device. As yet another example, a brooch or pin may include integrated circuitry and be a securing device to receive a display device. As yet another example, a necklace or earring may include integrated circuitry and be a securing device to receive a display device.

Figure 10A:
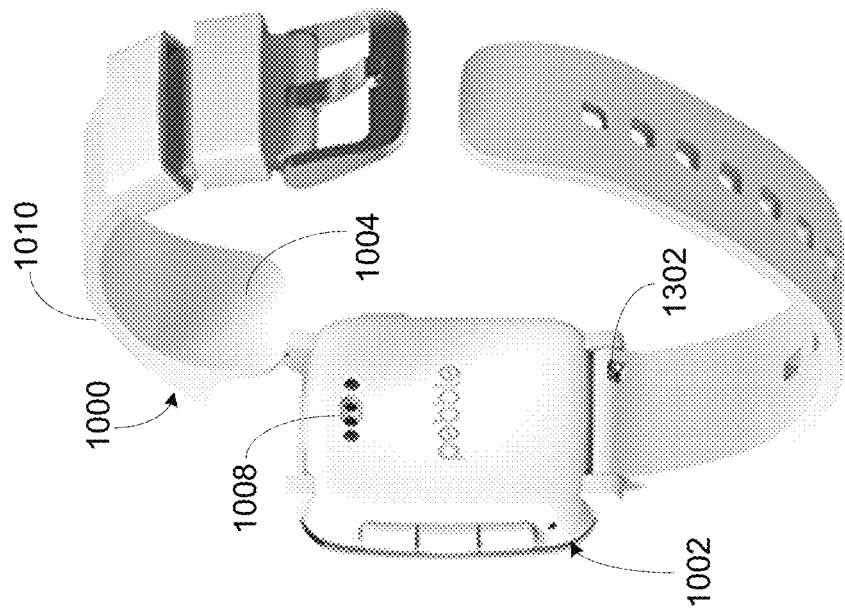
FIGS. 10A-10C are three views of an alternate embodiment of a wearable device created through connection of a securing device with a display device.
Figure 10B:
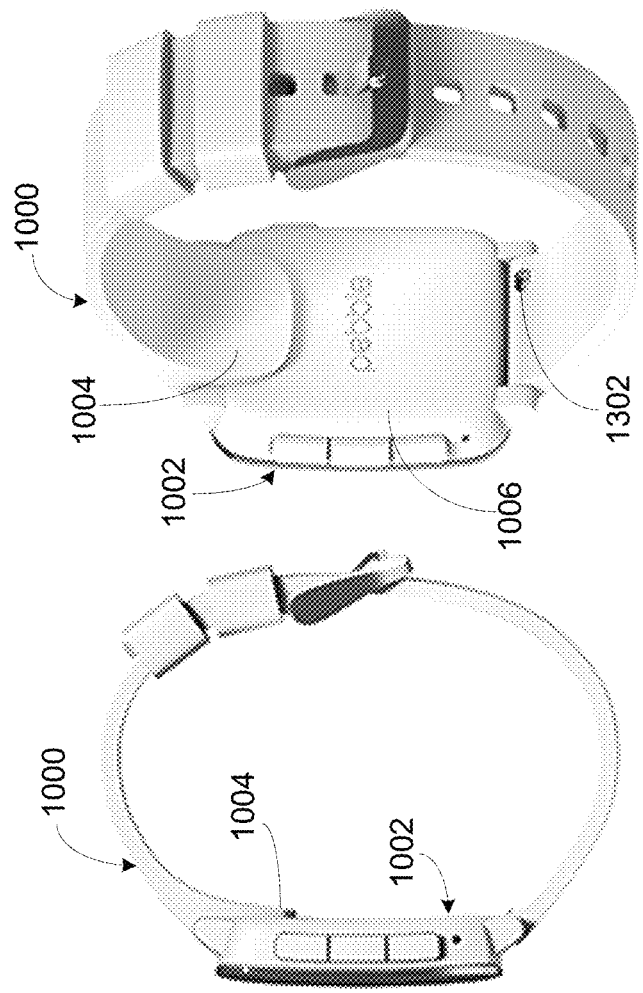
Figure 10C:
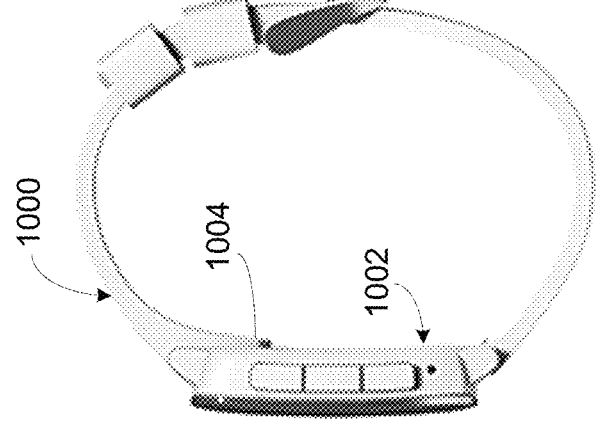
Figure 12:
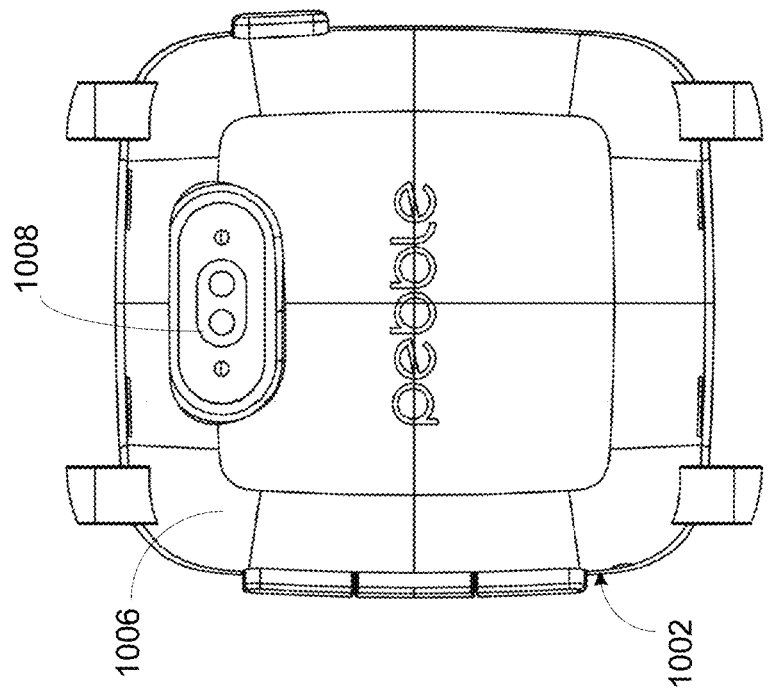
FIG. 12 is a back view of a display device of the embodiment of FIGS. 10A-10C.

FIGS. 10A-10C illustrate an alternate embodiment of a securing device, shown as a band 1000 attached to a display device, in this case a watch 1002. The band 1000 has an overlay portion 1004 which overlays the back 1006 of the watch 1002. The overlay portion 1004 is such that the overlay portion 1004 covers contacts 1008 on the back 1006 of the watch 1002. As the overlay portion 1004 is located behind the back 1006, as the watch 1002 is worn on a wrist, the overlay portion 1004 will be pressed into the back 1006 of the watch 1002 so that the contacts 1008 will be fully covered. If the clasp portion 1010 of the band 1000, which contains the overlay portion 1004', is rotated, the contacts 1008 may be exposed. FIG. 12 provides a back view of the watch 1002, showing the contacts 1008.

Figure 11:
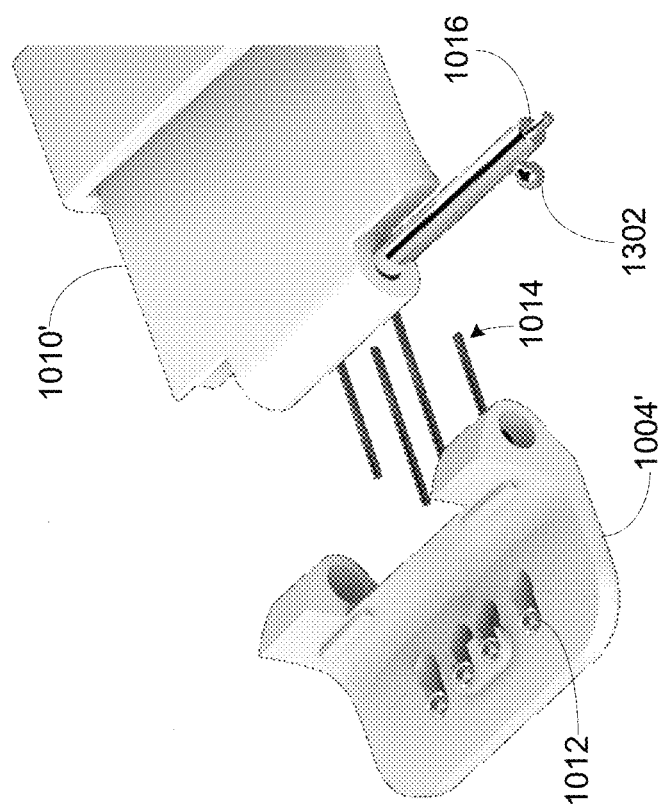
FIG. 11 is an enlarged, exploded view of the electrical connection element of FIGS. 10A-10C.

FIG. 11 illustrates a version of the clasp portion 1010, referred to as 1010', with an overlay portion 1004'. A series of wires 1014 are provided externally, rather than internally as shown in FIG. 10C, and the overlay portion 1004' is separated from the clasp portion 1010', being retained by a spring biased pin 1016, rather than being integral with the clasp portion, with the spring biased pin 1016 being located above the internal wires. The illustrated spring biased pin 1016 is a quick release pin and is described in more detail below. A series of pogo pins 1012 are located in the overlay portion 1004' and are located to align with the contacts 1008. As shown, two of the pogo pins 1012 and contacts 1008 are ground, one pogo pin 1012 and one contact 1008 is power, such as 5V and the final pogo pin 1012 and contact 1008 is single wire serial interface. The pogo pins 1012 are connected to the wires 1014 to allow access to the components, as discussed above, in the band 1000. Thus, when the watch 1002 is being worn, the pogo pins 1012 are in contact with the contacts 1008 and the function in the band 1000 is operational.

FIGS. 14A and 14B are views of power cables 1400 for use with a display device 202, like that shown in of FIGS. 10A-10C as 1002. A first end 1402 is configured to be plugged into a USB port to obtain power and ground to allow charging of the display device 1002. A second end 1404 has a series of pins 14o6 connected to the power and ground provided from the USB end 1402, the pins being arranged to mate with the contacts 1008 on the back 1006 of the display device 1002.

By having both the overlay portion 1004 and the second end 1404 having pins 1012, 1406 arranged to match the single set of contacts 1008, only a single set of contacts 1008 is needed to both charge the display device 1002 and communicate with the circuitry in the securing device 1000. When the display device 1002 is being worn, as stated above, the overlay portion 1004 is in connected to the contacts 1008. When the display device 1002 is not being worn and the clasp portion 1010 is rotated as mentioned above, clearance is provided to allow the power cable 1400 to be used to charge the display device 1002. This provides a very simple way to both provide additional functions as described above and to charge the device.

FIGS. 13A-13C illustrate more details of the spring biased pin 1016. The spring biased pin 1016 is different from a normal spring pin used to attach a watch band to a watch as it includes a projection 1302 for use to retract a protruding pin 1304. The projection 1302 is simply slid toward the center of the spring biased pin 1016 in a slot 1306. This retracts the protruding pin 1304, allowing the securing device to be very simply removed from the display device. A spring (not shown) contained inside the spring biased pin 1016 in a normal manner keeps the protruding pin 1304 in contact with a recess in the display device so that the securing device is attached. In the embodiment of FIGS. 13B and 13C, the protrusion 1302 is provided to the top of the band through an opening 1308. In the embodiment of FIGS. 10B and 10C the protrusion 1302 is provided on the bottom side of the band. The protrusion 1302 may be made flush with the surface of the securing device.

The spring biased pin 1016 may be used with the various embodiments where the securing device contains circuitry as described above, as the protrusion 1302 allows very simple operation to remove the securing device. A normal spring pin is difficult to remove, often requiring specialized tools, making changing a band challenging. By being easily removable the securing device can readily be changed should the user desire, which would permit securing devices capable of supporting different functions, such as using a battery for extended life, or adding a GPS sensor for more accurate user tracking.

It will also be understood that the above description is intended to be illustrative, and not restrictive. For example, the above-described embodiments may be used in combination with each other and features of one embodiment may be utilized with other embodiments. Many other embodiments will be apparent to those of ordinary skill in the art upon reviewing the above description. For example, the securing device may be implemented in other wearable technologies other than watches, such as wearable necklaces, ear rings, etc. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, while specific types of circuitry, plastics, metals, etc. have been mentioned throughout this specification, it would be understood that any known circuitry, plastic, metal, etc. may be suitable for use with the presently disclosed invention.

The invention claimed is:

1. A device comprising:
 a flexible band comprising:
  a flexible outer layer made of a pliable material extending across the flexible band;
  a flexible inner layer embedded within the outer layer and comprising flexible electronic circuitry, wherein the flexible electronic circuitry includes:
   an integrated display viewable through an opening in the flexible outer layer, and
   one or more sensors for health monitoring.

2. The device of claim 1, wherein the device further comprises a plurality of modules, wherein each module of the plurality of modules is capable of communicating with another module of the plurality of modules.

3. The device of claim 2, wherein each module of the plurality of modules is interchangeable with another module of the plurality of modules.

4. The device of claim 2, wherein each module of the plurality of modules includes corresponding flexible electronic circuitry capable of communicating with the flexible inner layer.

5. The device of claim 2, wherein the flexible outer layer covers the plurality of modules.

6. The device of claim 2, wherein each module of the plurality of modules contains a corresponding portion of the flexible inner layer.

7. The device of claim 6, wherein a module of the plurality of modules includes the integrated display viewable through the opening in the flexible outer layer.

8. The device of claim 1, wherein the integrated display viewable through the opening in the flexible outer layer includes at least one of a plurality LEDs and an LCD.

9. The device of claim 1, wherein the the opening in the flexible outer layer comprises at least one of a window and a translucent material.

10. The device of claim 1, wherein the one or more sensors for health monitoring provide one or more of a heart rate, a blood pressure, a skin temperature, or a skin resistance.

11. The device of claim 1, wherein the device is a securing strap device.

12. A flexible band comprising:
 a flexible outer layer made of a pliable material extending across the flexible band;
 a flexible electronic circuit embedded within the flexible outer layer, wherein the flexible electronic circuit comprises:
  an integrated display viewable through the flexible outer layer; and
  at least one of one or more sensors for health monitoring, Global Positioning System (GPS) circuitry, and an interface for wireless communication, wherein the integrated display viewable through the device layer is configured to communicate using the flexible electronic circuit material.

13. The device layer of claim 12, wherein the flexible electronic circuit includes one or more sensors for health monitoring that are configured to provide one or more of a heart rate, a blood pressure, a skin temperature, or a skin resistance.

14. The device layer of claim 12, wherein the integrated display viewable through the flexible outer layer comprises an LED.

15. The device layer of claim 12, wherein the flexible outer layer is a securing strap configured to be secured to a user.

16. A securing device comprising:
 a flexible outer layer made of a pliable material extending across the securing device;
 a flexible electronic circuitry layer embedded within the flexible outer layer, wherein the flexible electronic circuit comprises:

a first module comprising a first portion of the flexible electronic circuitry layer with a built-in display viewable through the flexible outer layer; and a second module comprising a second portion of the flexible electronic circuitry layer one or more sensors for health monitoring, wherein:

the first module and the second module are physically and electronically coupled; and the first module is configured to communicate with the second module using the first portion of the flexible electronic circuitry layer and the second portion of the flexible electronic circuitry layer to determine a functionality of the second module.

17. The securing device of claim 16, wherein the one or more sensors for health monitoring provide one or more of monitoring a heart rate, pulse, blood pressure, skin temperature, skin resistance, and glucose level.

18. The securing device of claim 16, wherein the first module is capable of reconfiguring itself based on the functionality of the second module.

19. The securing device of claim 16, wherein one of the first module and the second module may be disconnected from the securing device without changing a functionality of the other one of the first module and second module.

20. The securing device of claim 16, wherein the second portion of the flexible electronic circuitry layer includes Global Positioning System (GPS) circuitry.

* * * * *